(12) United States Patent
Murphy

(10) Patent No.: US 12,042,617 B2
(45) Date of Patent: Jul. 23, 2024

(54) DELIVERY SYSTEM FOR DELIVERING A DRUG DEPOT TO A TARGET SITE UNDER IMAGE GUIDANCE AND METHODS AND USES OF SAME

(71) Applicant: Kieran P. Murphy, Toronto (CA)

(72) Inventor: Kieran P. Murphy, Toronto (CA)

(73) Assignee: Kieran P. Murphy, Toronto (CA)

(*) Notice: Subject to any disclaimer, the term of this patent is extended or adjusted under 35 U.S.C. 154(b) by 12 days.

(21) Appl. No.: 18/127,710

(22) Filed: Mar. 29, 2023

(65) Prior Publication Data

US 2023/0248955 A1 Aug. 10, 2023

Related U.S. Application Data

(62) Division of application No. 16/273,613, filed on Feb. 12, 2019, now abandoned.

(Continued)

(51) Int. Cl.
*A61M 37/00* (2006.01)
*A61B 17/34* (2006.01)
(Continued)

(52) U.S. Cl.
CPC ..... *A61M 37/0069* (2013.01); *A61B 17/3403* (2013.01); *A61K 9/0021* (2013.01);
(Continued)

(58) Field of Classification Search
CPC ............ A61M 37/0069; A61M 31/002; A61B 17/3403; A61B 2017/00924; A61B 2017/3413
See application file for complete search history.

(56) References Cited

U.S. PATENT DOCUMENTS 3,721,997 A 3/1973 Mundt
3,984,696 A 10/1976 Collica et al.
(Continued)

FOREIGN PATENT DOCUMENTS

CA 2471958 A1 6/2003
DE 3405837 A1 10/1985
(Continued)

OTHER PUBLICATIONS

U.S. Appl. No. 16/273,613, Delivery System For Delivering a Drug Depot to a Target Site Under Image Guidance and Methods and Uses of Same, filed Feb. 2019.
(Continued)

*Primary Examiner* — James D Ponton
*Assistant Examiner* — Hong-Van N Trinh
(74) *Attorney, Agent, or Firm* — PERRY + CURRIER INC.

(57) ABSTRACT

A delivery system for delivering a drug depot to a site within a patient, the system comprising: a cannula; a delivery stylet configured and dimensioned to be receivable by and slidable forwardly and backwardly within the cannula including to a position wherein a distal portion of the stylet protrudes beyond the distal end of the cannula; a drug depot retainable by the stylet at the distal end of the stylet, the drug depot being visualizable by a diagnostic imaging beam or modality; and an actuator for ejecting the drug depot from the stylet to a site within the body using fluid pressure. Also disclosed are methods using, and uses of, the delivery system, including for treating scoliosis.

15 Claims, 10 Drawing Sheets

Related U.S. Application Data

(60) Provisional application No. 62/629,769, filed on Feb. 13, 2018.

(51) Int. Cl.
| | | |
|---|---|---|
| *A61K 9/00* | (2006.01) | |
| *A61M 5/178* | (2006.01) | |
| *A61M 5/31* | (2006.01) | |
| *A61M 5/32* | (2006.01) | |
| *A61M 31/00* | (2006.01) | |
| *A61B 17/00* | (2006.01) | |
| *A61B 90/00* | (2016.01) | |
| *A61M 5/315* | (2006.01) | |

(52) U.S. Cl.
CPC .......... *A61M 5/178* (2013.01); *A61M 5/3129* (2013.01); *A61M 5/3297* (2013.01); *A61M 31/002* (2013.01); *A61B 2017/00924* (2013.01); *A61B 2017/3413* (2013.01); *A61B 2090/3925* (2016.02); *A61B 2090/3966* (2016.02); *A61F 2310/00023* (2013.01); *A61K 9/0085* (2013.01); *A61M 2005/311* (2013.01); *A61M 5/31565* (2013.01); *A61M 2205/32* (2013.01)

(56) References Cited

U.S. PATENT DOCUMENTS

| | | | |
|---|---|---|---|
| 4,062,518 A | 12/1977 | Stivender et al. | |
| 4,258,722 A | 3/1981 | Sessions et al. | |
| 4,391,276 A | 7/1983 | Lazarus et al. | |
| 4,465,069 A | 8/1984 | Barbier et al. | |
| 4,533,356 A | 8/1985 | Bengmark et al. | |
| 4,610,671 A | 9/1986 | Luther | |
| 4,655,226 A | 4/1987 | Lee | |
| 4,686,962 A | 8/1987 | Haber et al. | |
| 4,732,933 A | 3/1988 | Maeda et al. | |
| 4,733,665 A | 3/1988 | Palmaz | |
| 4,739,762 A | 4/1988 | Palmaz | |
| 4,776,337 A | 10/1988 | Palmaz | |
| 4,795,458 A | 1/1989 | Regan | |
| 4,940,458 A | 7/1990 | Cohn | |
| 4,994,066 A | 2/1991 | Voss | |
| 5,037,427 A | 8/1991 | Harada et al. | |
| 5,058,577 A | 10/1991 | Six | |
| 5,064,435 A | 11/1991 | Porter | |
| 5,067,957 A | 11/1991 | Jervis | |
| 5,084,022 A | 1/1992 | Claude | |
| 5,102,417 A | 4/1992 | Palmaz | |
| 5,147,308 A | 9/1992 | Singer | |
| 5,169,386 A | 12/1992 | Becker et al. | |
| 5,211,165 A | 5/1993 | Dumoulin et al. | |
| 5,242,455 A | 9/1993 | Skeens et al. | |
| 5,250,035 A | 10/1993 | Smith et al. | |
| 5,292,339 A | 3/1994 | Stephens et al. | |
| 5,311,883 A | 5/1994 | Sherman | |
| 5,335,663 A | 8/1994 | Oakley et al. | |
| 5,403,341 A | 4/1995 | Solar | |
| 5,444,871 A | 8/1995 | Lopez | |
| 5,482,043 A | 1/1996 | Zulauf | |
| 5,492,130 A | 2/1996 | Chiou | |
| 5,499,418 A | 3/1996 | Tan et al. | |
| 5,522,881 A | 6/1996 | Lentz | |
| 5,522,882 A | 6/1996 | Gaterud et al. | |
| 5,531,737 A | 7/1996 | Schade | |
| 5,545,150 A | 8/1996 | Danks et al. | |
| 5,546,961 A | 8/1996 | Harrison | |
| 5,549,439 A | 8/1996 | Ploem | |
| 5,549,635 A | 8/1996 | Solar | |
| 5,556,414 A | 9/1996 | Turi | |
| 5,562,726 A | 10/1996 | Chuter | |
| 5,575,798 A | 11/1996 | Koutrouvelis | |
| 5,590,655 A | 1/1997 | Hussman | |
| 5,591,195 A | 1/1997 | Taheri et al. | |
| 5,592,952 A | 1/1997 | Bohn | |
| 5,607,467 A | 3/1997 | Froix | |
| 5,609,629 A | 3/1997 | Fearnot et al. | |
| 5,615,690 A | 4/1997 | Giurtino et al. | |
| 5,638,819 A | 6/1997 | Manwrring et al. | |
| 5,676,159 A | 10/1997 | Navis | |
| 5,693,015 A | 12/1997 | Walker et al. | |
| 5,702,682 A | 12/1997 | Thompson | |
| 5,725,572 A | 3/1998 | Lam et al. | |
| 5,735,892 A | 4/1998 | Myers et al. | |
| 5,741,333 A | 4/1998 | Frid | |
| 5,746,765 A | 5/1998 | Kleshinski et al. | |
| 5,772,669 A | 6/1998 | Vrba | |
| 5,782,764 A | 7/1998 | Werne | |
| 5,788,626 A | 8/1998 | Thompson | |
| 5,788,707 A | 8/1998 | Del Toro et al. | |
| 5,797,952 A | 8/1998 | Klein | |
| 5,800,517 A | 9/1998 | Anderson et al. | |
| 5,810,870 A | 9/1998 | Myers et al. | |
| 5,824,045 A | 10/1998 | Alt | |
| 5,857,997 A | 1/1999 | Cimino et al. | |
| 5,861,033 A | 1/1999 | Martakos et al. | |
| 5,876,448 A | 3/1999 | Thompson et al. | |
| 5,892,238 A | 4/1999 | Huttner et al. | |
| 5,899,935 A | 5/1999 | Ding | |
| 5,902,254 A | 5/1999 | Magram | |
| 5,906,618 A | 5/1999 | Larson, III | |
| 5,908,405 A | 6/1999 | Imran et al. | |
| 5,922,020 A | 7/1999 | Klein et al. | |
| 5,925,074 A | 7/1999 | Gingras et al. | |
| 5,957,974 A | 9/1999 | Thompson et al. | |
| 5,980,565 A | 11/1999 | Jayaraman et al. | |
| 5,989,280 A | 11/1999 | Euteneuer et al. | |
| 6,010,529 A | 1/2000 | Herweck et al. | |
| 6,059,759 A | 5/2000 | Mottola et al. | |
| 6,086,610 A | 7/2000 | Duerig | |
| 6,120,536 A | 9/2000 | Ding et al. | |
| 6,126,654 A | 10/2000 | Giba et al. | |
| 6,146,418 A | 11/2000 | Berman | |
| 6,179,878 B1 | 1/2001 | Duerig et al. | |
| 6,236,875 B1 | 5/2001 | Bucholz | |
| 6,241,734 B1 | 6/2001 | Scribner et al. | |
| 6,270,523 B1 | 8/2001 | Herweck et al. | |
| 6,283,125 B1 | 9/2001 | McNeirney et al. | |
| 6,285,902 B1 | 9/2001 | Kienzie et al. | |
| 6,298,110 B1 | 10/2001 | Ning | |
| 6,315,791 B1 | 11/2001 | Gingras et al. | |
| 6,325,538 B1 | 12/2001 | Heesch | |
| 6,352,561 B1 | 3/2002 | Leopold et al. | |
| 6,355,058 B1 | 3/2002 | Pacetti et al. | |
| 6,374,937 B1 | 4/2002 | Galando et al. | |
| 6,379,302 B1 | 4/2002 | Kessman et al. | |
| 6,400,979 B1 | 6/2002 | Stoianovici et al. | |
| 6,412,851 B1 | 7/2002 | Burks et al. | |
| 6,423,089 B1 | 7/2002 | Gingras et al. | |
| 6,428,557 B1 | 8/2002 | Hilaire | |
| 6,447,540 B1 | 9/2002 | Fontaine et al. | |
| 6,450,937 B1 | 9/2002 | Mercereau et al. | |
| 6,453,185 B1 | 9/2002 | O'Keefe | |
| 6,456,684 B1 | 9/2002 | Mun et al. | |
| 6,475,234 B1 | 11/2002 | Richter | |
| 6,475,235 B1 | 11/2002 | Jayaraman | |
| 6,481,888 B1 | 11/2002 | Morgan | |
| 6,490,467 B1 | 12/2002 | Bucholz et al. | |
| 6,490,475 B1 | 12/2002 | Seeley et al. | |
| 6,511,471 B2 | 1/2003 | Rosenman et al. | |
| 6,530,933 B1 | 3/2003 | Yeung et al. | |
| 6,533,806 B1 | 3/2003 | Sullivan et al. | |
| 6,544,041 B1 | 4/2003 | Damadian | |
| 6,578,219 B1 | 6/2003 | Gabel et al. | |
| 6,585,677 B2 | 7/2003 | Cowan, Jr. et al. | |
| 6,585,755 B2 | 7/2003 | Jackson et al. | |
| 6,629,992 B2 | 10/2003 | Bigus et al. | |
| 6,635,064 B2 | 10/2003 | U et al. | |
| 6,656,213 B2 | 12/2003 | Solem | |
| 6,679,886 B2 | 1/2004 | Weikel et al. | |
| 6,689,125 B1 | 2/2004 | Keith et al. | |
| 6,716,238 B2 | 4/2004 | Elliott | |

(56) References Cited

U.S. PATENT DOCUMENTS

| | | | |
|---|---|---|---|
| 6,734,937 | B2 | 5/2004 | Nakasogi et al. |
| 6,740,113 | B2 | 5/2004 | Vrba |
| 6,857,778 | B2 | 2/2005 | Mun et al. |
| 6,932,787 | B2 | 8/2005 | Cowan et al. |
| 6,961,606 | B2 | 11/2005 | DeSillets et al. |
| 7,391,042 | B2 | 6/2008 | Goldstein |
| 8,221,358 | B2 | 7/2012 | McKay |
| 8,246,571 | B2 | 8/2012 | Simonton et al. |
| 8,317,727 | B2 | 11/2012 | Peliks |
| 8,622,924 | B2 | 1/2014 | Speeg et al. |
| 8,628,475 | B2 | 1/2014 | Wang |
| 8,702,677 | B2 | 4/2014 | Simonton et al. |
| 8,715,223 | B2 | 5/2014 | McKay |
| 9,033,912 | B2 | 5/2015 | McKay |
| 9,149,293 | B2 | 10/2015 | Hardert et al. |
| 9,610,243 | B2 | 4/2017 | Clay et al. |
| 9,821,033 | B2 | 11/2017 | Murphy |
| 2001/0041928 | A1 | 11/2001 | Pavcnik et al. |
| 2002/0002383 | A1 | 1/2002 | Sepetka et al. |
| 2002/0022825 | A1 | 2/2002 | Saitou et al. |
| 2002/0040239 | A1 | 4/2002 | Murayama et al. |
| 2002/0052640 | A1 | 5/2002 | Bigus et al. |
| 2002/0077540 | A1 | 6/2002 | Kienzle, III |
| 2002/0111603 | A1* | 8/2002 | Cheikh ............... A61K 38/31 424/422 |
| 2002/0183610 | A1 | 12/2002 | Foley et al. |
| 2002/0183763 | A1 | 12/2002 | Callol et al. |
| 2002/0196906 | A1 | 12/2002 | Mun et al. |
| 2003/0004491 | A1 | 1/2003 | Tenhuisen et al. |
| 2003/0004563 | A1 | 1/2003 | Jackson et al. |
| 2003/0050574 | A1 | 3/2003 | Krueger |
| 2003/0055379 | A1 | 3/2003 | Rosiello |
| 2003/0181807 | A1 | 9/2003 | Murphy et al. |
| 2003/0181810 | A1 | 9/2003 | Murphy et al. |
| 2003/0204248 | A1 | 10/2003 | Murphy |
| 2004/0073286 | A1 | 4/2004 | Armstrong et al. |
| 2004/0082905 | A1 | 4/2004 | Solar et al. |
| 2004/0148000 | A1 | 7/2004 | Bilge |
| 2004/0176682 | A1 | 9/2004 | Murphy |
| 2004/0176833 | A1 | 9/2004 | Pavcnik et al. |
| 2004/0176835 | A1 | 9/2004 | Vrba |
| 2004/0199120 | A1* | 10/2004 | Lohr ............... A61M 37/0069 604/59 |
| 2004/0241094 | A1 | 12/2004 | Chung et al. |
| 2006/0104999 | A1 | 5/2006 | Chung et al. |
| 2006/0134144 | A1 | 6/2006 | Chung et al. |
| 2008/0182282 | A1 | 7/2008 | Markman et al. |
| 2009/0131908 | A1* | 5/2009 | McKay ............... A61B 17/3468 604/60 |
| 2010/0029908 | A1 | 2/2010 | Sing et al. |
| 2010/0106132 | A1 | 4/2010 | Simonton |
| 2010/0106133 | A1 | 4/2010 | Simonton et al. |
| 2010/0106137 | A1 | 4/2010 | Simonton et al. |
| 2011/0022028 | A1 | 1/2011 | McKay |
| 2011/0040279 | A1* | 2/2011 | Walsh ............... A61M 37/0069 604/522 |
| 2011/0184037 | A1 | 7/2011 | Haddock et al. |
| 2011/0196499 | A1 | 8/2011 | Boucher et al. |
| 2012/0053561 | A1 | 3/2012 | Simonton et al. |
| 2012/0101577 | A1 | 4/2012 | Lee |
| 2012/0101578 | A1 | 4/2012 | Lee |
| 2012/0253228 | A1 | 10/2012 | Schembre et al. |
| 2012/0323219 | A1 | 12/2012 | Huntoon |
| 2013/0216602 | A1 | 8/2013 | Clay et al. |
| 2013/0237910 | A1 | 9/2013 | Shetty et al. |
| 2015/0148775 | A1 | 5/2015 | Clay et al. |
| 2016/0022704 | A1 | 1/2016 | McKay et al. |
| 2016/0022973 | A1 | 1/2016 | Clay et al. |
| 2016/0022974 | A1 | 1/2016 | Clay et al. |
| 2016/0022975 | A1 | 1/2016 | Clay et al. |
| 2017/0304555 | A1 | 2/2017 | Misle et al. |
| 2017/0143950 | A1 | 5/2017 | Koch et al. |

FOREIGN PATENT DOCUMENTS

| | | |
|---|---|---|
| DE | 3918736 A1 | 12/1990 |
| EP | 0578998 A1 | 1/1994 |
| EP | 0797988 A2 | 10/1997 |
| EP | 0809998 A2 | 12/1997 |
| EP | 0872220 A1 | 10/1998 |
| EP | 0947204 A3 | 10/1999 |
| EP | 0966920 A2 | 12/1999 |
| EP | 1155689 A2 | 11/2001 |
| EP | 1362603 A2 | 11/2003 |
| WO | WO-9826731 A2 | 6/1998 |
| WO | WO-0024338 | 5/2000 |
| WO | WO-0040159 A1 | 7/2000 |
| WO | WO-03094798 A1 | 11/2003 |
| WO | WO-2006023315 A2 | 3/2006 |
| WO | WO-2008115526 A2 | 9/2008 |

OTHER PUBLICATIONS

ISA/CA, International Search Report and Written Opinion, May 14, 2019, re PCT International Patent Application No. PCT/IB2019/051130.

Murphy, Kieran P. "Kit for Image Guided Surgical Procedures", U.S. Appl. No. 10/373,835, filed Feb. 27, 2003.

Grieb, Christian, "International Search Report", PCT Application No. PCT/US2015/055499 mailed Feb. 2, 2016.

Montes, Jose M. et al., "Stereotactic computed Tomographic-Guided Aspriation and Thrombolysis of Intracerebral Hematoma" Stroke Apr. 2000; vol. 31: pp. 834-840.

Final Rejection dated Dec. 10, 2015 for Related U.S. Appl. No. 14/709,220.

International Preliminary Report on Patentability dated Apr. 18, 2017 for PCT International Application No. PCT/US2015/055499.

Murphy, Kieran P. "Biopsy Needle", U.S. Appl. No. 14/516,218, filed Oct. 16, 2014.

Chouquette et al. Direct Selenium X-Ray Detector for Fluoroscopy, R&F, and Radiography, 2000, In Medical Imaging 2000: Physics of Medical Imaging, Proceedings of SPIE vol. 3977, pp. 128-136.

Summerscales, John, Non-Destructive testing of fibre-reinforced plastic compoites, vol. 2; Elsevier Science Publishers Ltd., 1990; p. 208.

Laasch, Dr. Hans-Ulrich et al., "Revision Notes for the FRCR Part 1", The Society of Radiologists in Training, 1999 (60 pages).

Park, Seung-Jung M.D. et al. "A Paclitaxel-Eluting Stent for the Prevention of Coronary Restenosis, " The New England Journal of Madicine, vol. 348:1537-1545, No. 16, Apr. 17, 2003.

Office Action dated Feb. 28, 2012 for U.S. Appl. No. 11/081,494.

Office Action for U.S. Appl. No. 13/047,226 dated Apr. 13. 2012.

International Search Report dated Feb. 2, 2016 for International Application No. PCT/US2015/055499.

Brem, H. et al. Biocompatibility of biodegradable, controlled-release polymer in the rabbit brain, http://www.ncbi.nlm.nih.gov:80/entrz/query.fcgi?cmnd=Retrieve&db=PubMed&list_uids=2772427&dopt=Abstract, last visited on Oct. 3, 2003 (1 page).

Schroeder, Stephen et al. Influence of Heart Rate on Vessel Visibility in Non-invasive Coronary anglography Using new Multislice Computed Tomography Experience in 94 patients Journal of Clinical Imaging 26 (2002). pp. 106-107.

Kak, A.C. et al., "Principles of Computerized Tomographic Imaging", Chapter 4 (Measurement of Projection Data-The Nondiffracting Case) pp. 113-134, IEEE, 1988 (22 pages).

Kovscek, Anthony R et al., "Stanford University Petroleum Research Institute Preliminary Twenty-Fourth Annual Report", Apr. 19-21, 2001 (68 pages).

Maintz, David et al., Revealing In-StentStenoses of the Liac Arteries: Comparison of Multidetector CT with MR Angiography and Digital Radiographic Anglography in a Phantom Mode AJR:179,p. 1319-1322 Nov. 2002.

Dolmatch, Bart, M.D. et al., Patency and Tissue Response Related to Two Types of Polytetrafluoroethylene-Covered Stents in the Dog, Journal of Vascular and Interventional Radiology vol. 7,No. 5 Sep.-Oct. 1996, pp. 642-649.

(56) References Cited

OTHER PUBLICATIONS

Weigel, Stefanie et al.—Thoracic Aortic Stent Graft: Comparison of Contract-enhanced MR Angiography and CT Angiography in the Follow-Up: Initial Results, Eur Radiol (2003) 13: 1628-1634, Feb. 2003.
Knez A. et al., Detection of coronary calcinosis with multislice spiral computerized tomography: an alternative to electron beam tomography Z Kardiol. Aug. 2002:91(8):642-9.
Ohnesorge B, et al., "Cardiac imaging with rapid, retrospective ECG synchronized multilevel spiral CT." Der Radiologe 40.2 (2000): 111-117 with English abstract.
Drake et al., The Shunt Book, COPYRGT. 1995 Blackwell Science Inc. Massachusetts.
Rodenwaldt, Jens "Multislice Computed Tomography of the Coronary Arteries," Eur Radiol (2003) 13:748-757, Jan. (2003).
Kopp A F et al., Cardiac multidetector-row CT: first clinical results of retrospectively ECG-gated spiral with optimized temporal and spatial resolution, Rofo Fortschr Geb Rontgenstr Neuen Bildgeb Verfahr. May 2000; 172(5):429-35.
Tamargo, Rafael J. et al. The Intracerebral Administration of Phenytoin Using Controlled-Release Polymers Reduces Experimental Seizures in Rats, Epilepsy Research 48, p. 145-155 (2002).
Achenbach, S. et al., Non-invasive coronary angiography with electron beam tomography: methods and clinical evaluation in post-PTCA follow-up Z Kardiol., Feb. 1997; 86(2):121-30.
Becker C R et al., Methods for quantification of coronary artery calcificatins with electron beam and conventional CT and pushing the spiral CT envelope: new cardiac applications. Int J Cardiovasc Imaging, Jun. 17, 2001;(3):203-11.
Kopp, A F. et al., Non-invasive coronary angiography with high resolution multidetector-row computed tomography. Results in 102 patients. Eur Heart J. Nov. 23, 2002;(21): 1714-25.
Google, Google's Cache of http://www.bicetre.neuroradio.net/french/journal/menu.htm.at http://www.google.com/search?q=cachelU20QRBv7hYC; www.bicetre.neuroradio.net/french/journal/menu.htm=MCTA+angiography&hi=en&ie+UTF8,Index MARS 2002 (5 pages).
Foy, Jonette, "Drug Eluting Stents: Pre-Clinical Standards & Recommended Studies".FDA/SIR Device Forum Meeting, Nov. 2002.
Gabikian, Patrik, MD et al. "Stroke: Prevention of Experimental Cerebral Vasospasm by Intracranial Delivery of Nitric Oxide Donor From Controlled-Relase Polymer," http://www.neurosurgery-online/fulltext/4904/0945/NURO49040945-doc.html, vol. 49, No. 4, Oct. 2001 (11 pages).
Achenbach S. et al., Noninvasive coronary angiography by retrospectively ECG-gated multislice spiral CT. Circulation. Dec. 5, 2000:102(23):2823-8.
Hahnel, Stefan., et al., "Small-Vessel Stents for Intracranial Angioplasty: In Vitro Comparison of Different Stent Designs and Sizes by Using CT Angiograph" AJNR Am J Neuroradiol 24:1512-1516, Sep. 2003.
Strotzer, Michael, MD et al., "Appearance of Vascular Stents in Computed Tomographic Angiography: In Vitro Examination of 14 Different Stent Types, "Investigative Radiology, vol. 36 (11) p. 652-658, Nov. 2001 (6 pages).
Antezana, DF et al., "High-dose Ibuprofen for reduction of striatal infarets during middle cerebral artery occlusion in rats, http://www.nc:bi .nlrn .nih.gov:80/entrez/query Jcgi?cmd'-"PubMed&list-uids+ 12691413&dopt"Abstract; last visited1 on Oct. 1, 2003 (2 pages).
Thai, Quoc-Anh, BA et al., Inhibition of Experimental Vasospasm in Rats with the Periadventital Administration of Ibprofen Using Controlled-Release Polymers published by American Heart Association; pp. 140-147 Jan. 1999.
Wang, Paul P. et al"Local Drug Delivery to the Brain," Advanced Drug Delivery Review 54 (2002) pp. 987-1013.
Brem, Henry, et al. "Polymer-Based Drug Delivery to the Brain" Science & Nedicine, Inc. vol. 3 No 4, p. 1-11, Jul./Aug. 196 (11 pages).
Langer R. Brem, et al. "Biocompatibility of Polymeric deivery system for Macromolecules, "http://www.ncbi,nlm.nlh.gov:80/entrez/query.fcgi?cmd=Retrieve&db=PubMedlist-uids+2772427&dopt= Abstract, last visited on Oct. 3, 2003 (1 page).
Written Opinion dated Feb. 2, 2016 for International Application No. PCT/US2015/055499.
Tierney, Travis S. et al., "Prevention and Reversal of Experimental Posthemorrhagic Vasospasm by the Oeriadventital Administration of Nitric Oxide From a Controlled-release Polymer," http://www.neurosurgery-online/fulltext/4904/0945/NURO49040945-doc.html, vol. 49, No. 4, Oct. 2001 (11 pages).
Fossa Medical, Welcome to Fossa Medical.com@URL <http://www.fossamedical.com/news.htm. from Sep. 9, 2005 (retrieved on Sep. 18, 2008).
Stone Sweeper (r) Kidney Stone Removal Device: The Clear Path to Ureteral Patency—Insertion Instructions, at URL <http://www.fossamedical.com/pdfs/sweepersurgicaltechnique.pdf>, 2004 (retriedved on Sep. 18, 2008),.
Naff, Neal J. et al. "Treatment of Intraventricular Hemorrhage with Urokinase Effects on 30 Day Survival"; Stroke, Apr. 2000; vol. 31, pp. 841-847.
Miyake, Hiroji MD; et al."A New Ventriculoperitoneal Shunt with a Telemetric Intracranial Pressure Sensor: Clinical Experience in 94 Patients with Hydrocephalus", Neurosurgery. 40(5): 931-935, May 1997.
Gailloud, P et al., " Vertebrobasilar Stroke as a Late Complication of a Blalock-Taussing Shunt" Willey-Liss, Inc. 2002, pp. 231-234 (4 pages).
Canadian Office Action dated Mar. 9, 2011 for Application No. 2,455,439.
Golzarian, J. "Imaging after Endovascular Repair of Abdominal Aortic Aneurysm", Abdominal Imaging 28, p. 236-243 (2003).
Heldman, Allan W. et al. "Paclitaxel Stent Coating inhibits Neointimal Hyperplasia at 4 weeks in Porcine Model of Coronary Restenosis," published by the American Heart Association Inc., pp. 228902295, May 2001.
EPO, Communication pursuant to Article 94(3) EPC, Aug. 1, 2019, re European Patent Application No. 15787809.1.
Murphy, Kieran P. "Apparatus for Use in a Surgical Procedure," U.S. Appl. No. 13/858,609, filed Apr. 8, 2013.
Munshi I. Lathrop D, et al. "Intraventricular Pressure Dunamics in Patients with Ventriculopleural Shunts: a Telemetric Study", Pediatric Neurosurgery, 1998; vol. 28: pp. 67-69.
Non-Final Rejection dated Jul. 7, 2016 for U.S. Appl. No. 15/183,126.
Murphy, Kieran P. "A Sterile Drape for Attachment to an Imaging Machine," U.S. Appl. No. 13/190,830, filed Jul. 26, 2011.
Murphy, Kieran P. "Kit for Image Guided Surgical Procedures", U.S. Appl. No. 11/081,494, filed Mar. 17, 2005.
Moses et al., Sirolimus Eluting Stents Versus Standard Stents in Patients with Stenosis of the Coronary Artery, New England Journal of Medicine, p. 1315-1323, Oct. 2, 2003 vol. 349.
Lee, Y et al. "Synthesis of 188 Re-labelled long chain alkyl diaminedithiol for therapy of liver cancer". Nuclear Medicine Communications, Mar. 2002, vol. 23, issue 3 pp. 237-242.
Wang, Shenguo et al., "Biodegradable Ploylactone-Family Plolymers and Their Applications in Medical Field", Nov. 17-30, 2005, 8th Arab International Conference on Polymer Science & Technology, Nov. 17-30, 2005, 15 pages.
Google, Google's Cache of http://www.google.ca/search ?q=% houndsfield+unit%22&ie+UTF-8&OE=UTF8&hi=en&meta=, Mar. 21, 2003 (60 pages).
Office Action dated Feb. 28, 2012 for U.S. Appl. No. 11/081,494.
Mahnken A H, Sinha AM, Wildberger J E, Krombach GA. Schmitz-Rode T, Gunther R W, The Influence of Motion Artifacts Conditioned by Reconstruction, on the Coronary Calcium Score in Multislice Spiral CT, Rofo Fortschr Geb Rontgenstr Neuen Bildgeb Verahr, Oct. 2001; 173(10): 888-92.
Office Action dated Jul. 1, 2010 for U.S. Appl. No. 11/081,494.
Office Action dated Mar. 9, 2011 for Corresponding Canadian Patent Application No. 2455439.
European Patent Application No. EP 04812874 Search Report dated Dec. 18, 2008.

\* cited by examiner

//DELIVERY SYSTEM FOR DELIVERING A DRUG DEPOT TO A TARGET SITE UNDER IMAGE GUIDANCE AND METHODS AND USES OF SAME

CROSS-REFERENCE TO RELATED APPLICATIONS

This application claims priority to U.S. 62/629,769, filed Feb. 13, 2018, the entirety of which is incorporated herein by reference.

FIELD OF THE INVENTION

The present invention relates to devices or delivery systems for drug depots and methods for delivering drug depots to inside an animal, including humans.

BACKGROUND OF THE INVENTION

Drugs may be delivered to patients by a variety of methods including oral, intravenous, intramuscular, inhalation, topical, subcutaneous delivery or delivery directly or locally to the treatment site (e.g., intrathecally, intraspinally, intraarticularly, etc.). The method of delivery chosen depends, among other things, upon the condition being treated, desired therapeutic concentration of the drug to be achieved in the patient and the duration of drug concentration that must be maintained.

Drug depots have been developed which allow a drug to be introduced or administered to sites beneath the skin of a patient (e.g., subcutaneously or intramuscularly) so that the drug is slowly released over a long period of time. Such drug depots allow the drug to be released from the depot in a relatively uniform dose over a time period.

Drug depot delivery devices or systems have been developed for implanting drug depots. One prior art device has a handle for one-handed implantation of the drug depot, a small needle containing the drug depot to be implanted, and a rod positioned within the needle for pushing the drug depot out of the needle. Once the needle containing the drug depot has been inserted at the site of implant, a spring-loaded trigger on the handle is activated which causes the needle to be automatically withdrawn by a spring leaving the implanted drug depot in place. Unfortunately, it is not possible to control the motion of the needle in these devices because the needle will automatically retract upon activation of the trigger. The complex spring loaded propelling system and trigger of these devices increase the chances that the device will jam and fail to eject the drug depot when required, or deposit the drug depot in a less than optimal site.

Other prior art devices also suffer from inaccurate placement of the drug depot due to the limited control over where the drug is deposited. Therefore, new drug depot devices or delivery systems are needed, which can allow more accurate and precise implantation of a drug depot with minimal physical and psychological trauma to a patient.

SUMMARY OF THE INVENTION

Accordingly, the invention provides, according to a first aspect, a delivery system for delivering a drug depot to a site within a patient, the system comprising:
  a hollow cannula having a proximal end and a distal end;
  a delivery stylet having a proximal end, a distal end, a lumen extending between the proximal and distal ends of the delivery stylet, and a distal portion at the distal end of the delivery stylet, the delivery stylet being configured and dimensioned to be receivable by and slidable forwardly and backwardly within the cannula including to a position wherein said distal portion protrudes beyond the distal end of the cannula; and
  an actuator for ejecting the drug depot from the stylet to a site within the body, said actuator having a fluid (e.g. liquid) delivery mechanism in fluid communication with an interior of the stylet and being effective to create pressure within the stylet sufficient to eject the drug depot therefrom.

In certain embodiments, the delivery system further comprises a drug depot to be administered to a patient. The drug depot may be packaged separately or retained by the stylet at the distal end of the stylet. When retained in the stylet, the drug depot may have a portion inside the stylet and a portion protruding from the distal end of the stylet. Furthermore, the drug depot may be visualizable by a diagnostic imaging beam or modality (e.g. computed tomography (CT), ultrasound, x-ray, magnetic resonance imaging (MRI), and fluoroscopy). For example, the drug depot may incorporate a radiographic marker that allows the drug depot to be visualized under a diagnostic imaging beam. The radiographic marker may be selected from the group consisting of barium, calcium phosphate, bismuth, iodine, tantalum, tungsten, metal beads, and mixtures thereof.

In some embodiments, the delivery system may further comprise a solid stylet configured and dimensioned to be receivable inside the cannula to provide rigidity thereto, whereby the cannula, with the solid stylet received therein, is effective to pierce tissue of a patient, prior to the use of the delivery stylet.

The delivery stylet may have a hub at the proximal end thereof, and the actuator may be releasably attachable to the hub.

The actuator of the system may be a syringe having a barrel with a distal portion thereof configured to be attachable to the hub of the delivery stylet, and a plunger slidable within the barrel. In some embodiments, the syringe is a Luer lock syringe and the hub of the delivery stylet has external threads complementary to internal threads of the Luer lock of the syringe.

The fluid (e.g. liquid) delivery mechanism may deliver liquid selected from the group consisting of an anaesthetic (e.g. Marcaine), Depo-Medrol (methylprednisolone), dexamethasone, and mixtures thereof.

In some embodiments, at least one of the cannula and delivery stylet comprises a radiopaque material or ultrasound responsive topography to provide increased contrast relative to the absence of the material of topography under a diagnostic imaging beam.

The invention also provides, in accordance with a second aspect, a method of delivering a drug depot to a site within a patient using the delivery system according to the first aspect, comprising:
  a. inserting the cannula with solid stylet received into a target tissue of a patient under image guidance;
  b. removing the solid stylet from the cannula and inserting the delivery stylet into the cannula until the distal portion of the delivery stylet emerges from the distal end of the cannula;
  c. positioning the drug depot under image guidance by moving the delivery stylet forwards or backwards until the drug depot is positioned at a desired location; and
  d. actuating the actuator to expel the drug depot from the delivery stylet.

The method can be used to treat scoliosis according to the additional teachings of U.S. Pat. No. 9,821,033 for an invention entitled Method of Treating Scoliosis, the contents of which are incorporated herein by reference. That is, the present delivery system can be used to treat scoliosis by delivering a drug depot comprising a therapeutically effective or acceptable amount of a growth modulator into a first epiphyseal growth plate of a first vertebra for altering the growth of the first epiphyseal growth plate to correct or compensate for disproportionate growth.

BRIEF DESCRIPTION OF THE DRAWINGS

The invention may be better understood with reference to the following description and drawings in which.

DETAILED DESCRIPTION OF EMBODIMENT

For the sake of clarity and to avoid ambiguity, certain terms are defined herein as follows.

The term "comprising" means "including without limitation." Thus, a system, device, or component comprising a list of elements may include additional elements not expressly recited. The term "consisting of" means "including the listed elements and such additional elements as may be normally present in the recited elements." Elements that would normally be present in a recited element will be apparent to the person of ordinary skill in the art. For example, a "needle" will necessarily have a proximal and a distal end. The term "consisting essentially of" means "consisting of" (as defined herein) the listed elements plus such additional elements as would not materially affect (positively or negatively) the basic and novel properties of the invention. By "basic and novel properties" is meant the ability of the systems, devices and methods according to the invention to deliver a drug depot to a desired site within the body.

The numerical values set forth herein are reported as precisely as possible. However, any numerical value inherently may contain errors resulting from the standard deviation found in standard measurement techniques. Therefore, unless the context indicates otherwise, all numerical values recited herein are to be understood as being modified by the term "about." Furthermore, the numerical parameters set forth herein may vary depending upon the desired properties sought to be obtained by the present invention. Without limiting the application of the doctrine of equivalents to the scope of the claims, each numerical parameter should (at least) be construed in light of the number of reported significant digits and ordinary rounding techniques. Moreover, all ranges disclosed herein are to be understood to encompass any and all subranges subsumed therein. For example, a range of "1 to 10" includes any and all subranges having a minimum value of equal to or greater than 1 and a maximum value of equal to or less than 10, e.g., 2-4, 5.5-10, etc.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

When used herein, the term "patient" can refer to animals, including, without limitation, humans.

The headings below are not meant to limit the disclosure in any way; embodiments under any one heading may be used in conjunction with embodiments under any other heading.

Figure 1:
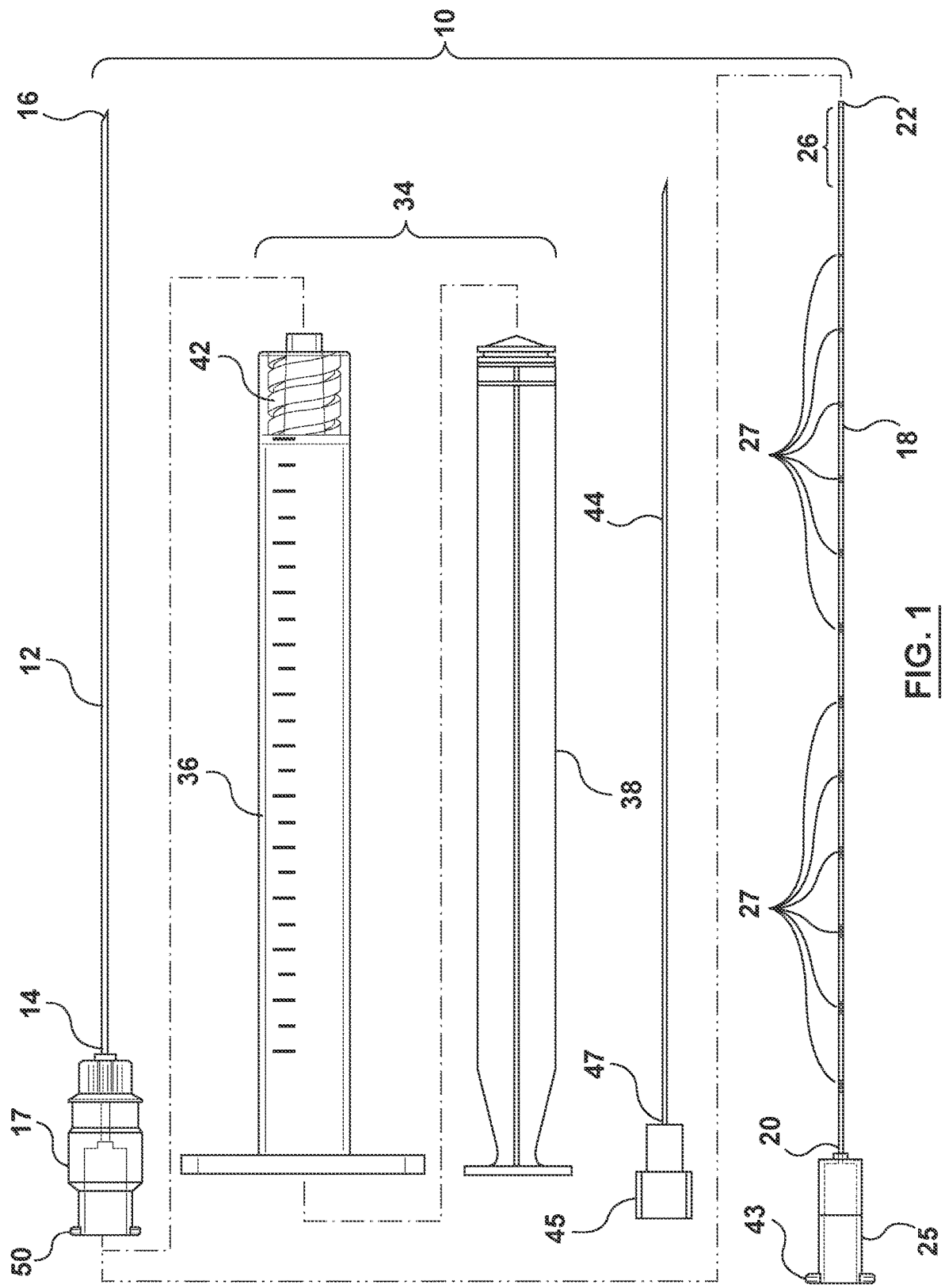
FIG. 1 shows components of a delivery system for delivering a drug depot pursuant to one embodiment of the invention.

Referring now primarily to FIG. 1, a delivery system 10 for delivering a drug depot (not shown) to a site within a patient is shown. The system 10 comprises a hollow cannula 12 having a proximal end 14 and a distal end 16. A plastic hub 17 is attached to the cannula 12 at the proximal end 14 to allow a user to grasp and manipulate the cannula 12. The distal end 16 of the cannula 12 is bevelled to facilitate piercing of tissue, as will be described below. The cannula 12 is designed to cause minimal physical and psychological trauma to the patient and made of a low density material, in this case, carbon fiber, to reduce beam hardening artifacts when visualized under an imaging beam of a CT scanner (not shown).

Figure 9:
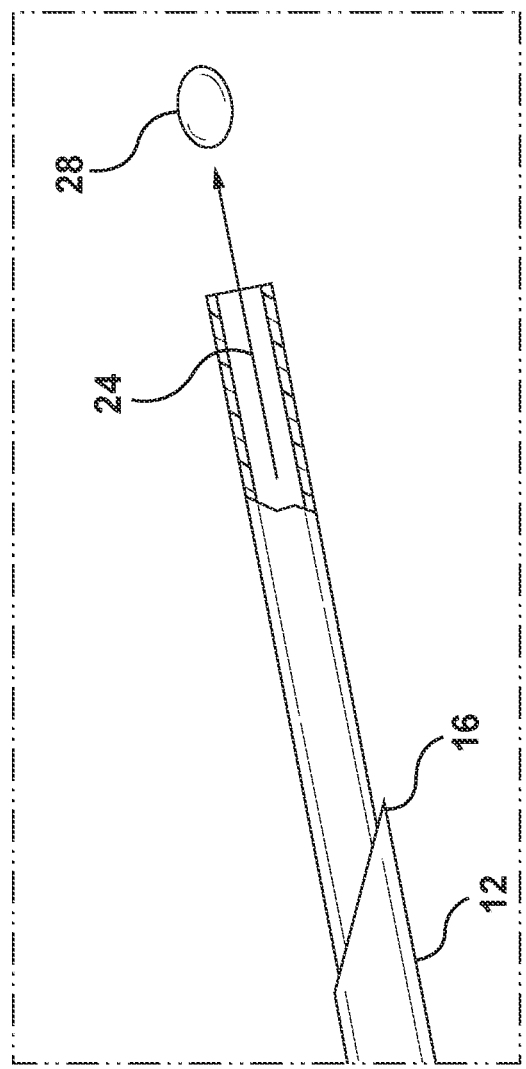

The system 10 also includes a plastic delivery stylet 18 having a proximal end 20, a distal end 22, a lumen 24 (referenced in FIGS. 6 and 9) extending between the proximal and distal ends 20, 22. At the proximal end 20 is attached a plastic hub 25 for use in grasping and manipulating the delivery stylet 18. The delivery stylet 18 is longer than the cannula 12 and further dimensioned to be receivable by and slidable forwardly and backwardly within the cannula 12 including to a position wherein a distal portion 26 protrudes beyond the distal end 16 of the cannula 12 (as will be described further below).

Figure 5:
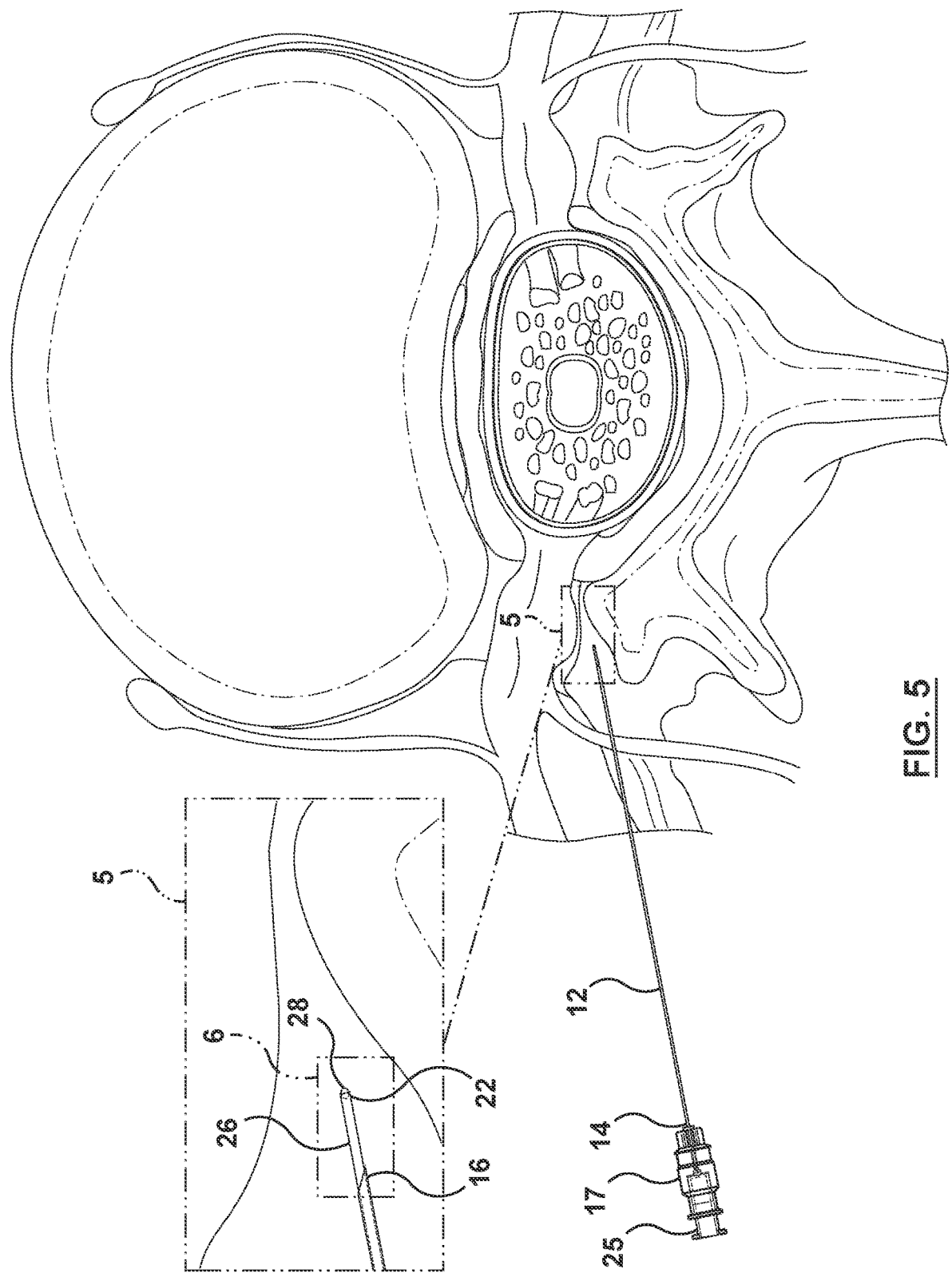
Figure 6:
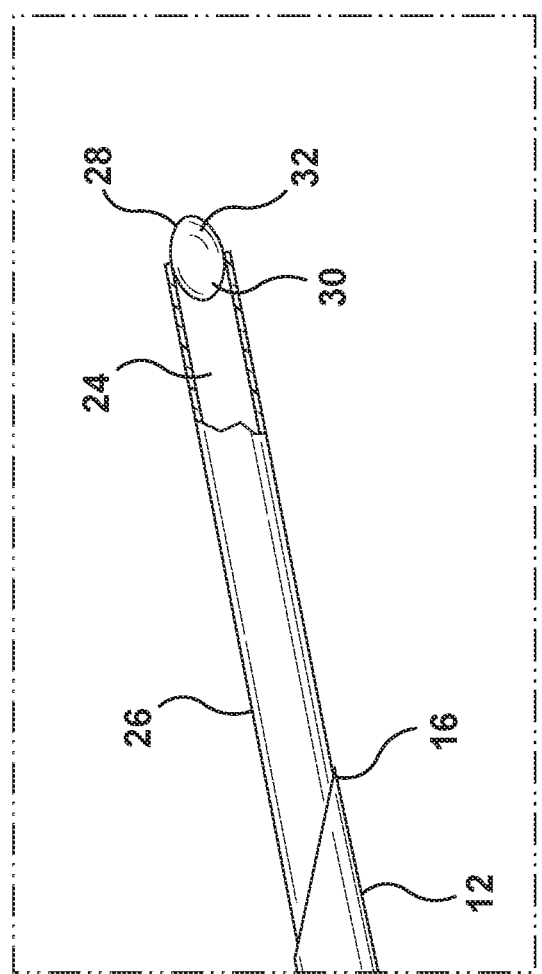

As best shown in FIGS. 5 and 6, a drug depot 28 is retained by the delivery stylet 18 at the distal end 22 of the stylet 18. Referring to FIG. 6, the drug depot 28 has a portion 30 inside the delivery stylet 18 and a portion 32 protruding from the distal end 22 of the delivery stylet 18. As will be further described, the drug depot 28 can be visualized by a diagnostic imaging beam or modality, which in this embodiment, is a beam of a CT scanner.

The system 10 further includes an actuator, which, in this embodiment, is in the form of a syringe 34 comprising a barrel 36 and plunger 38. The plunger 38 is slidable within the barrel 36 to eject the drug depot 28 from the delivery stylet 18 using a fluid (in this case a liquid) in the barrel 36 to a site within the body (as will be further described below). The syringe 34 is a Luer lock syringe making it releasably attachable to a hub 25 of the delivery stylet 18 using internal screw threads 42 of the barrel 36 and external thread 43 of the hub 25.

The system 10 further comprises a solid plastic stylet 44 having a plastic hub 45 attached to a proximal end 47 thereof for use in grasping and manipulating the stylet 44. The solid stylet 44 is configured and dimensioned to be receivable inside the cannula 12 to provide additional rigidity thereto, whereby the cannula 12, with the solid stylet 44 received therein, can be used to pierce tissue of a patient prior to use of the delivery stylet 18, as will now be described with reference to FIGS. 2-10.

Figure 2:
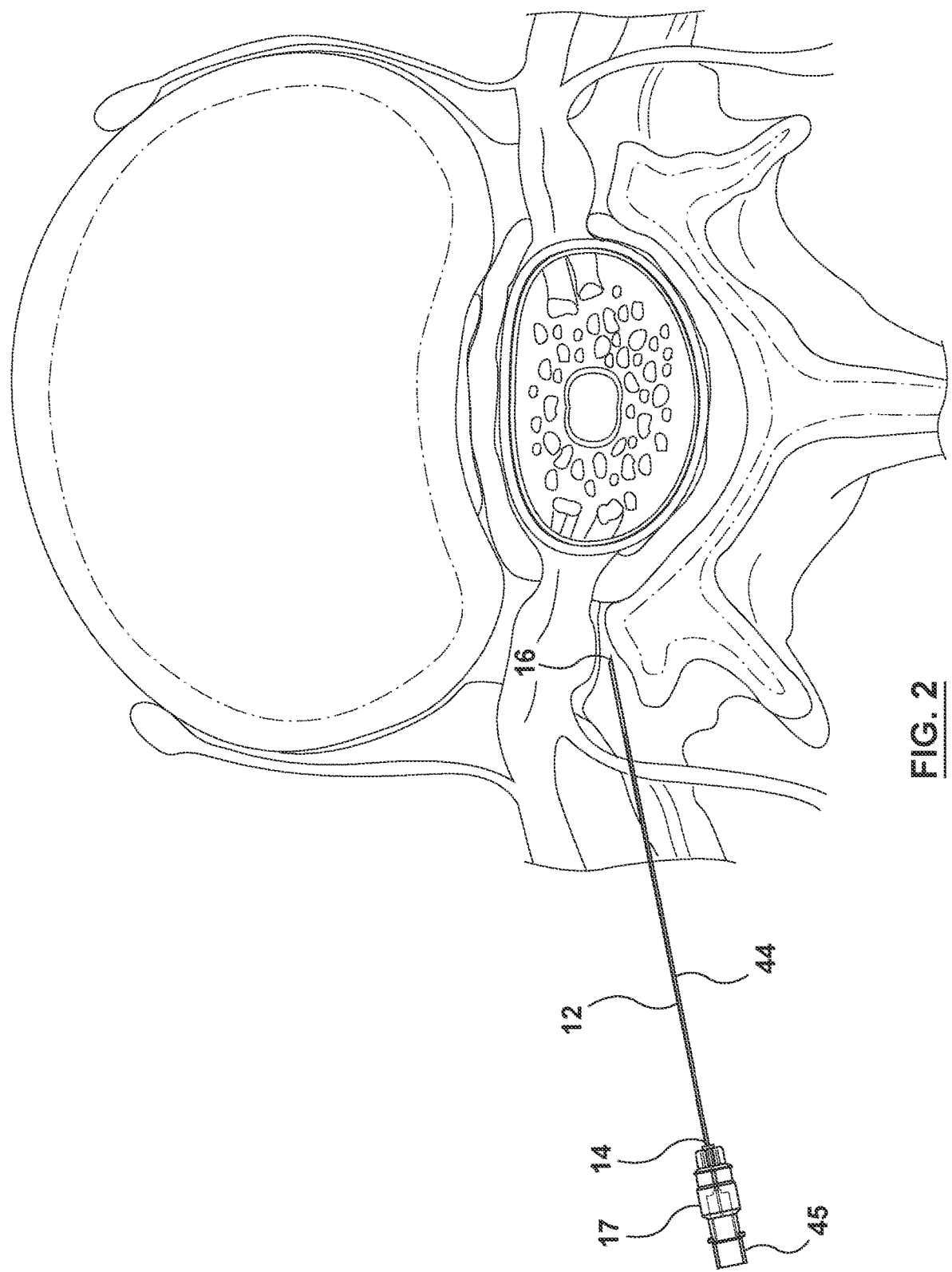
FIGS. 2-10 show the system in use at various stages of delivery of the drug depot to a site near the spinal column of a patient.
Figure 3:
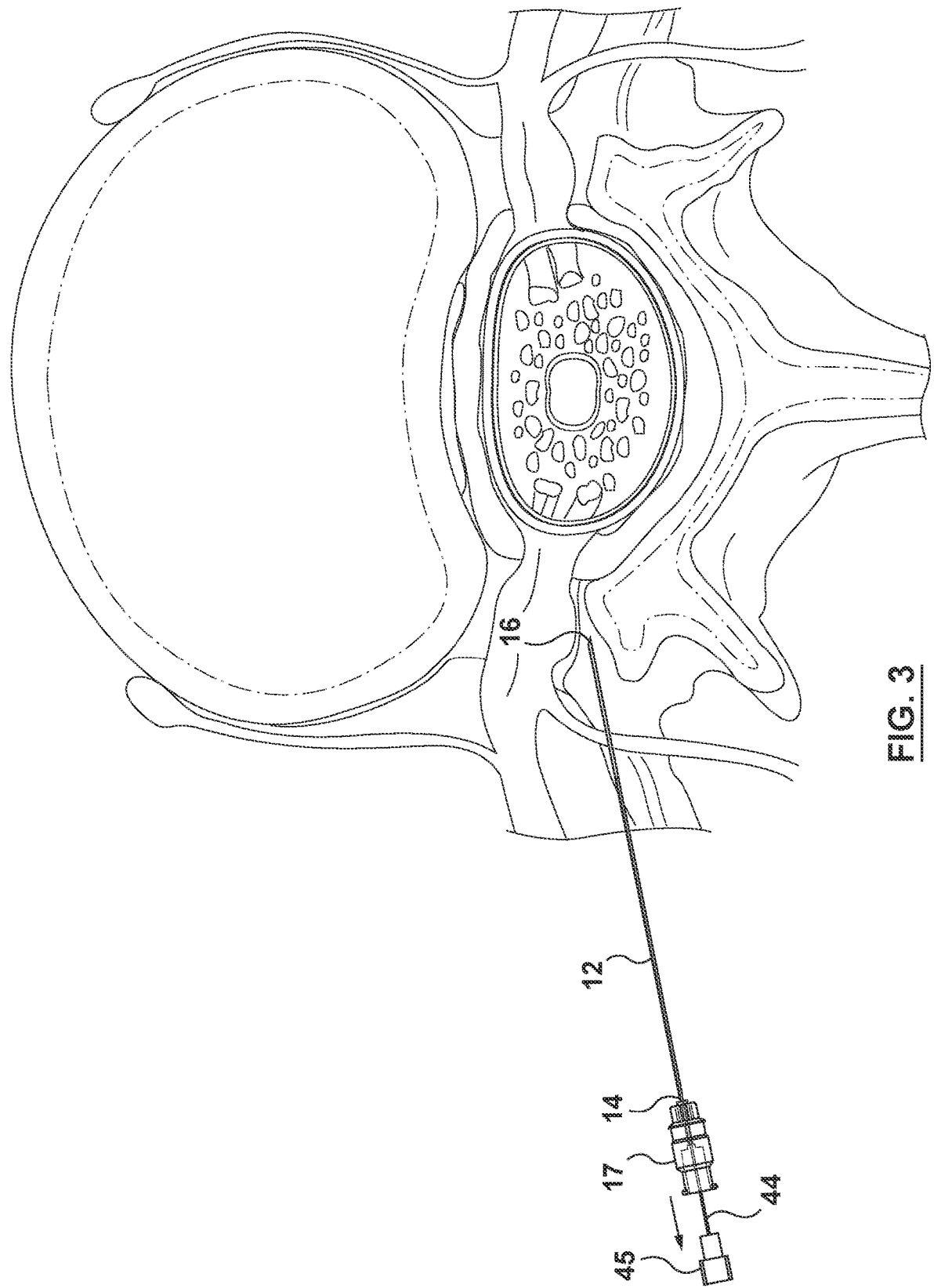
Figure 4:
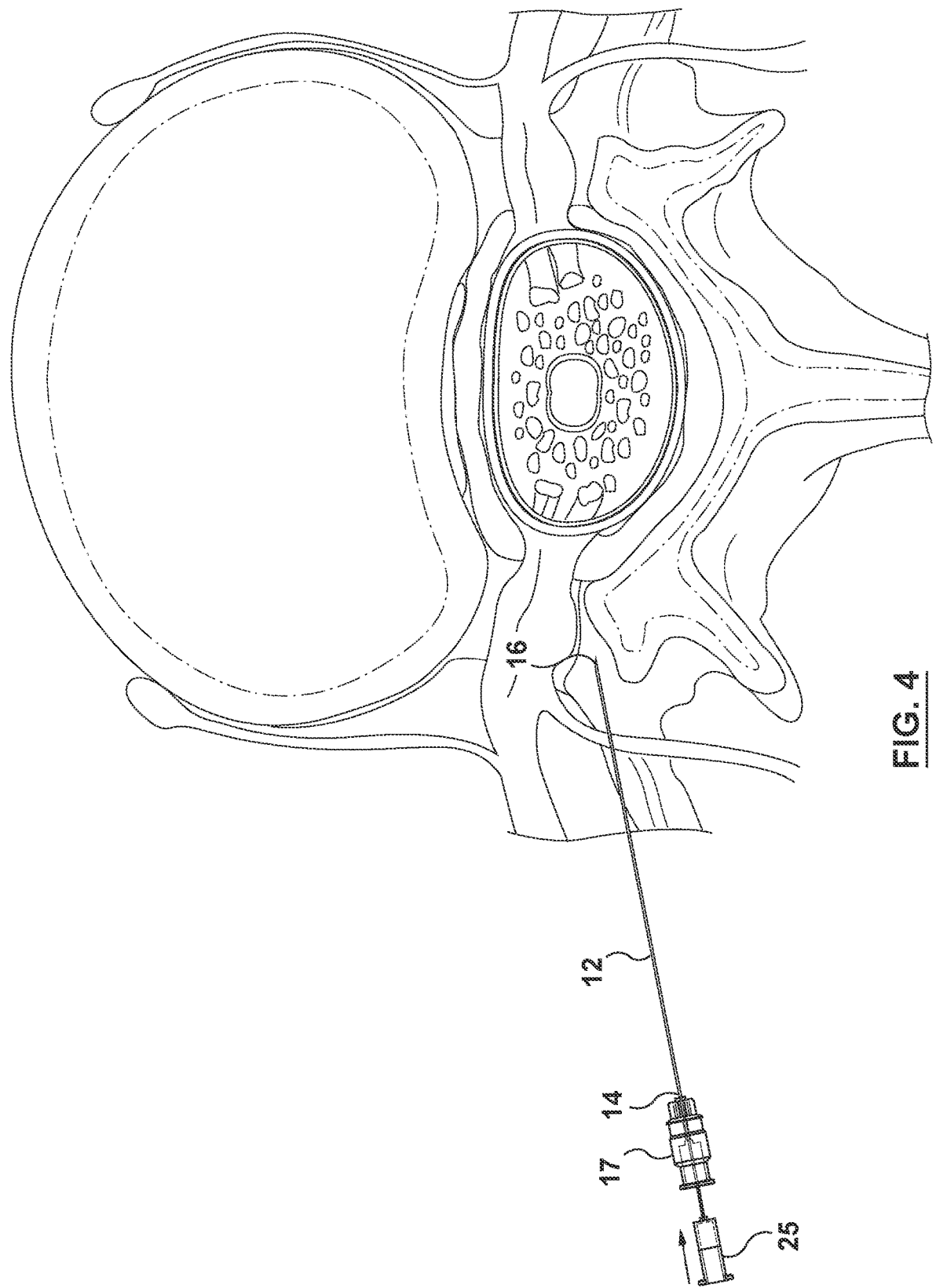
Figure 7:
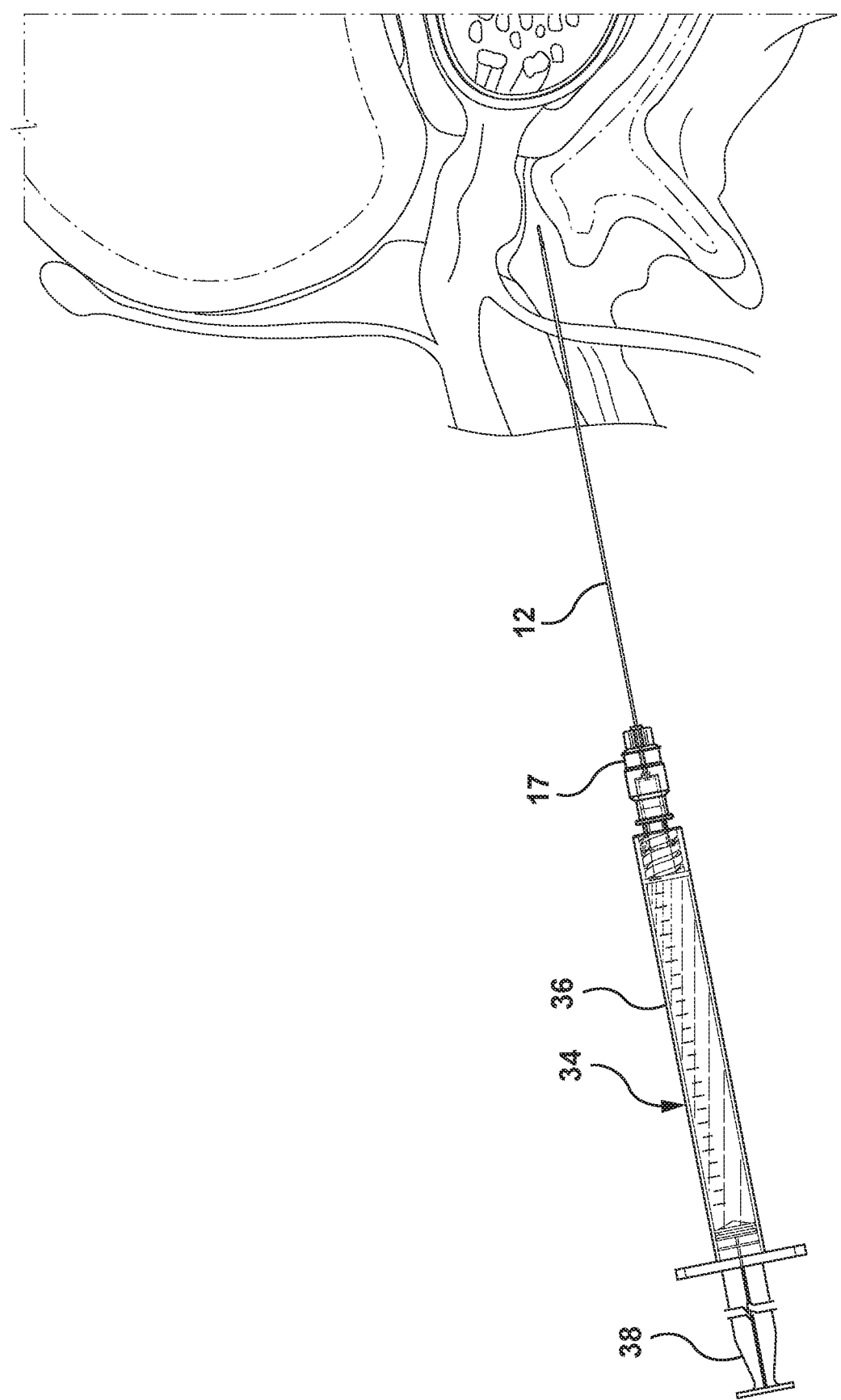

As shown in FIG. 2, during a procedure, the cannula 12 with the solid plastic stylet 44 seated therein is advanced through tissue of a patient until the distal end 16 of the cannula reaches a desired location within the patient, but can in other locations, e.g. along the path of the exiting nerve root or to the rear of the dorsal root ganglion. In this embodiment, the location is near the spinal column of the patient. Because of the materials used in the cannula and solid stylet, the combination can be visualized under an imaging beam of a CT scanner (not shown) with reduced beam hardening artifacts. This facilitates accurate placement of the cannula within the patient. Once the cannula is moved to the desired location, the solid stylet 44 is withdrawn (as shown in FIG. 3) and the delivery stylet 18 carrying the drug depot 28 is inserted into the cannula 12 (shown in FIG. 4) until the distal portion 26 of the delivery stylet 18 emerges from the distal end of the cannula 12 (as shown in FIG. 5). Referring to FIG. 7, physical markers 27 are placed at regular and predetermined, in this case 1 cm, intervals on the delivery stylet 18 and are used to determine the position of the delivery stylet 18 relative to the cannula 12 by inspecting the location of the markers relative to a proximal end 50 of the hub 17 of the cannula 12. The markers 27 are placed to allow the user to determine when the distal end 22 of the delivery stylet 18 will emerge from the distal end 16 of the cannula 12.

Figure 8:
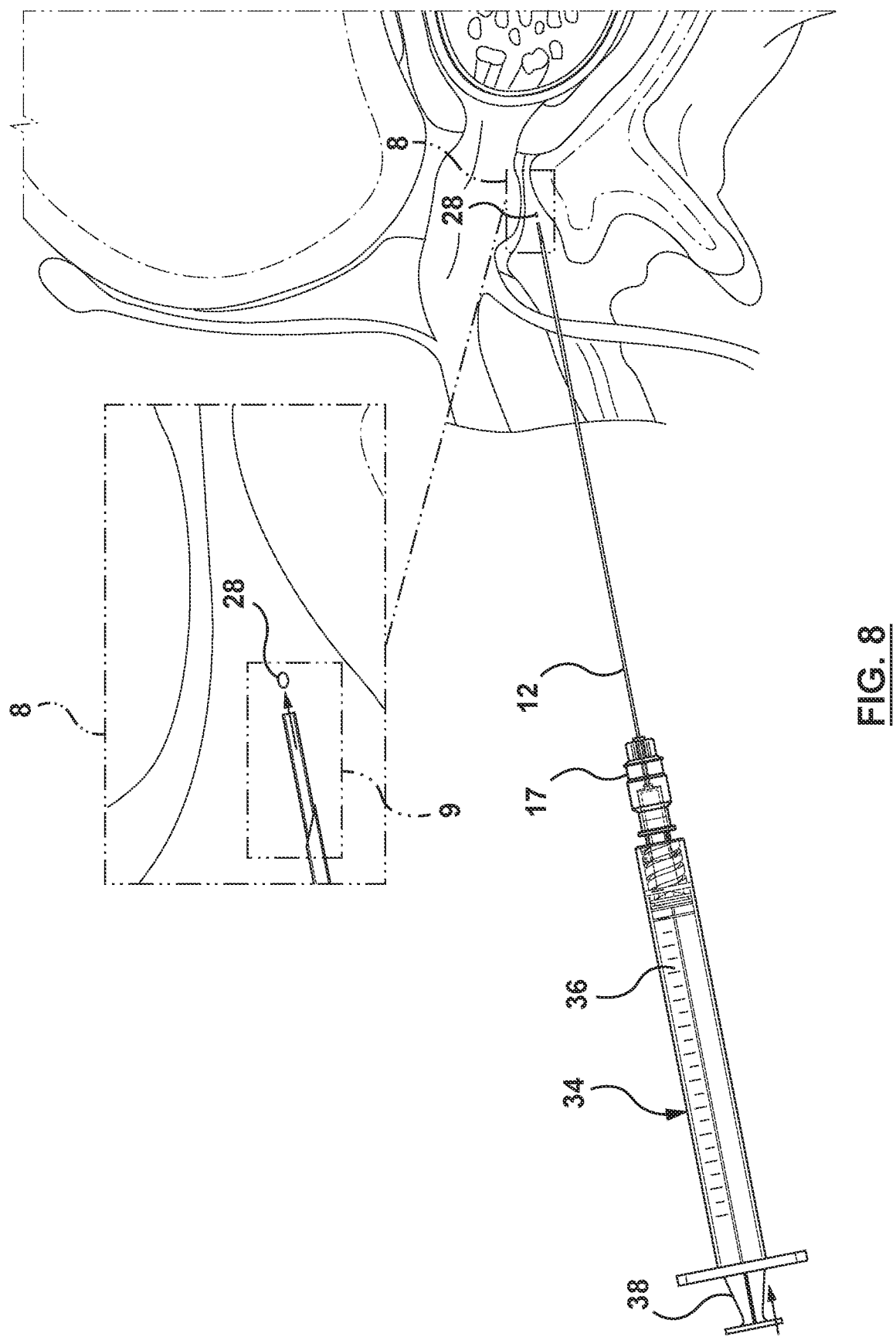
Figure 10:
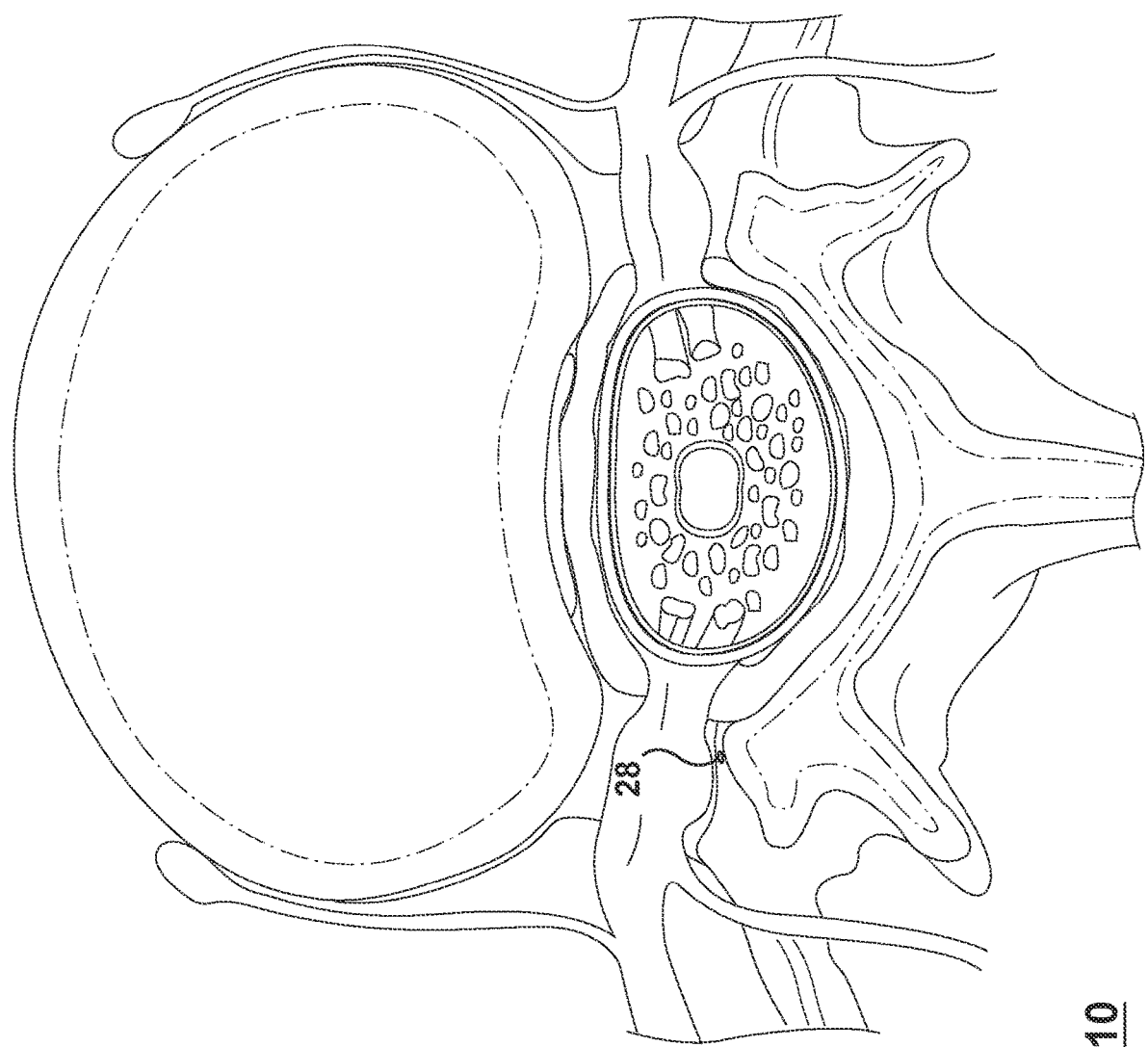

The areas denoted by reference numerals 5 and 6 in FIG. 5 are enlarged and shown in FIGS. 5 and 6 to better show the drug depot 28 carried by the distal end 22 of the delivery stylet 18. The drug depot 28 is in the form of a biodegradable pellet provided with a lyophilized powder coating containing a radiographic marker, in this case iodine, to allow the drug depot 28 to be visualized under a diagnostic imaging beam of a CT scanner. The coating also contains a therapeutic agent, in this case, clonidine, for use in treating pain (amongst other things). The user can position the drug depot 28 within the patient by moving the delivery stylet 18 back and forth within the cannula 12 until the drug depot 28 reaches the desired location based on the user's view of the drug depot 28 under the imaging beam. Once the drug depot 28 is in the desired location, the barrel 36 of the Luer lock syringe 34 carrying liquid, in this case, a saline solution comprising a mixture of 0.5 g/ml of Marcaine and 40 mg/ml of Depo-Medrol, is screwed onto the hub 40 of the delivery stylet 18, and the plunger 38 is advanced within the barrel 36 to expel the liquid through the lumen 24 of the delivery stylet 18 thereby depositing the drug depot 28 in the desired location in the neural foramen near the spinal column of the patient—see FIGS. 7, 8 and 9, wherein the areas denoted by reference numerals 8 and 9 in FIG. 8 are shown enlarged in FIG. 8 and * to between show the drug depot 28 being expelled from the distal end 22 of the delivery stylet 18. The syringe 34, cannula 12, and delivery stylet 18 are then withdrawn from the patient leaving the drug depot 28 in place near the spinal column (as shown in FIG. 10). After deposition, the radiographic marker of the drug depot 28 can be used to track movement and/or degradation of the drug depot 28 at the site over time.

In accordance with another aspect of the invention, there is provided a method for localized and/or targeted delivery of a drug to a patient to treat a disease or condition such as for example, scoliosis, rheumatoid arthritis, osteoarthritis, sciatica, carpal tunnel syndrome, cancer, inflammation and pain, such as lower back pain, sciatica, lower extremity pain, upper extremity pain, tissue pain and pain associated with injury or repair of cervical, thoracic, and/or lumbar vertebrae or intervertebral discs, rotator cuff, articular joint, TMJ, tendons, ligaments, muscles, and the like. The treatment of scoliosis can incorporate methods disclosed in U.S. Pat. No. 9,821,033 referenced above.

Treating or treatment of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

"Localized delivery" includes delivery to tissue within close proximity to a target site in the tissue, e.g. within about 10 cm or about 5 cm from the target site. "Targeted delivery" includes delivery to the target site.

It will be appreciated that numerous variations can be made to the embodiment described above as will be described below.

Cannula and Stylets

The various embodiments, the materials used to make the cannula 12, stylets 18, 44 and hubs of the cannula, delivery stylet and solid stylet 17, 25, 45 may be the same or different materials. Examples of materials that can be used include but are not limited to polyurethane, polyurea, polyether (amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

The cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the cannula relative to the absence of the material or topography. To reduce or minimize beam hardening artifacts under a CT scan, low density materials (relative to stainless steel or steel) can be used.

The cannula may also include one or more tapered regions or have a tip style designed for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. Ideally, the cannula is packaged together with a sheath covering the distal end thereof prior to use to avoid unwanted needle sticks.

The dimensions of the cannula, among other things, will depend on the site for implantation. For example, the width of the epidural space is only about 3-5 mm for the thoracic region and about 5-7 mm for the lumbar region. Thus, the cannula can be designed for these specific areas. In various embodiments, the cannula may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina and implanting the drug depot.

The length of the cannula will vary depending on the specific application and may range from about 50 to 150 mm. For example, for epidural use, the cannula may be about 65 mm for use in children, about 85 mm for use in a standard adult, and about 110 mm for use in an obese adult patient. The thickness of the cannula will also depend on the specific application, including the site of implantation. The thickness includes, but is not limited to, from about 0.05 to about 1.655 mm. The gauge of the cannula may be the widest or smallest diameter or a diameter in between for insertion into a patient. The widest diameter is typically about 14 gauge, while the smallest diameter is about 22 gauge. In various embodiments, the gauge of the cannula is about 18 to about 22 gauge.

The delivery stylet and solid stylet will be dimensioned to be slidable within the cannula. The length of the delivery stylet will, in all cases be greater than the length of the cannula in order for the distal portion thereof to protrude from a distal end of the cannula when fully inserted therein. The markers on the delivery stylet can be placed at differing intervals, e.g. every 1 mm to 1 cm, along its length or along a portion of its length. For example, the markers can appear only along a proximal end portion of the delivery stylet to allow the user to determine the degree to which the delivery stylet is extending beyond the distal end of the cannula during a procedure.

Drug Depot

The drug depot comprises a physical structure to facilitate implantation and retention in a desired site (e.g., a synovial joint, a disc space, a spinal canal, soft tissue surrounding the spinal canal, or other tissue of the patient, etc.). The drug depot includes but is not limited to capsules, microspheres, particles, gels, matrices, wafers, pills, cartridges, pellets or other pharmaceutical delivery compositions provided that they can be shaped and sized so as to be receivable by the delivery stylet and slidable through the cannula of the delivery system of the invention.

In various embodiments, the drug depot is in the form of a pellet. Pellets include, but are not limited to, substantially spherical, rod shaped, square, oval shaped particles having, in various embodiments, an aspect ratio (the ratio of the length to the width of the pellet) which is less than about 4.0 to about 1.0.

Procedures for making pellets include, but are not limited to, extrusion-spheroidization, for spherical pellets where the active pharmaceutical ingredient (API) and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, cylindrical extrudate of uniform shape and size. The size of the opening in the screen or die dictate resultant pellet size. The extrudate is fed onto a rotating disk, which may be smooth or may contain a grid (waffled, grooved, etc.) and the extrudate breaks into small cylinders, which in time are rounded into spherically shaped solids. Subsequently, the pellets are dried to the desired residual moisture content, typically in a fluid bed dryer. Any oversized or undersized product is removed by sieving, and the resulting pellets have a narrow size distribution.

The drug depot also comprises a therapeutically effective amount of a drug. The term "drug" as used herein is generally meant to refer to any substance that alters the physiology of a patient. The term "drug" may be used interchangeably herein with the terms "therapeutic agent", and "active pharmaceutical ingredient". It will be understood that a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 1 cm, about 5 cm, or about 10 cm, from the implant site. A "therapeutically effective amount" is an amount such that when administered, the drug results in alteration of the biological activity, such as, for example, inhibition of inflammation, reduction or alleviation of pain, improvement in the condition, etc. The dosage administered to a patient can be a single dose or multiple doses depending upon a variety of factors, including the drug's pharmacokinetic properties, patient conditions and characteristics (sex, age, body weight, health, size, etc.), extent of symptoms, concurrent treatments, frequency of treatment and the effect desired.

Examples of drugs suitable for use in the drug depot, include, but are not limited to growth modulators (both positive and negative) such as those disclosed in U.S. Pat. No. 9,821,033, an anti-inflammatory agent, analgesic agent, or osteoinductive growth factor or a combination thereof. Anti-inflammatory agents include, but are not limited to, salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells, mesenchymal stem cells, or a combination thereof.

Suitable analgesic agents include, but are not limited to, acetaminophen, lidocaine, bupivicaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof. Analgesics also include agents with analgesic properties, such as for example, amitriptyline, carbamazepine, gabapentin, pregabalin, clonidine, or a combination thereof.

Other therapeutic agents which can be incorporated into the drug depot include NSAIDs, anti-tumour necrosis factor (anti-TNF), interleukins, byname, dexamethasone, and anaesthetic agents.

In various embodiments, the drug can be layered on the solid core of the pellet by solution or suspension layering or by powder layering techniques, as are known in the art.

The drug depot may comprise a biopolymer that is biodegradable or non-biodegradable. For example, the drug depot can comprise a non-biodegradable body in the form of a porous hollow chamber filled with the therapeutic agent alone or incorporated into a degradable polymer. It may be desirable to make the body non-degradable to be able to retrieve it after it has released its contents. Non-limiting examples of suitable biodegradable materials for the pellet body include polyorthoesters (POE), polylacticglycolic acid (PLGA) polysacharides (Saber technology), polycapralactone, polyfumarate, tyrosine polycarbonate, etc. The body may be solid, and the therapeutic agent may be dispersed throughout the material that forms the body. The dispersal of the therapeutic agent may be even throughout the body. Alternatively, the concentration of the therapeutic agent may vary throughout the body. As the biodegradable material of the body degrades at the site, the therapeutic agent is released.

The drug depot may also comprise a biopolymer that may provide for immediate release, sustained release, or controlled release of the drug(s). Examples of suitable sustained release biopolymers include but are not limited to poly (alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO—PPO-PEO (pluronics), PEO—PPO-PAA copolymers, PLGA-PEO-PLGA, or combinations thereof.

In one embodiment, the pellet is made using a core of biodegradable material, such as, for example, polyglactin, polylactone, polylactide, etc. The core is then coated with a thin layer of the drug, such as an anti-inflammatory agent, analgesic agent, etc. by solution, suspension, or powdered layering until the desired potency is achieved.

In various embodiments, the drug pellets can be different sizes, for example, from a length of from about 0.5 mm to 5 mm and have a diameter of from about 0.01 to about 2 mm. The layer or layers will each have a layer thickness of from about 0.005 to 1.0 mm, such as, for example, from about 0.05 to about 0.75 mm.

Radiographic markers that can be incorporated in the drug depot include iodine, barium, calcium phosphate, bismuth, tantalum, tungsten, metal beads (e.g. gold, silver), and mixtures thereof. Instead of or in addition to a radiographic marker, the drug depot can be provided with a certain topography to allow the drug depot to be visualised under ultrasound. Depending on the nature of the radiographic marker and/or topography, a variety of diagnostic imaging procedures can be used including X-ray imaging, magnetic resonance imaging (MRI), ultrasound and fluoroscopy.

The fluid used to eject the drug depot can be a gas (eg. air) or a liquid, including any pharmaceutically acceptable liquid such as a pharmaceutically acceptable saline solution alone or in combination with a pharmaceutically effective amount of an anaesthetic, e.g. Marcaine. Marcaine can be used in an amount of about 0.5, 1, or 2 v/v %, Depo-Medrol (methylprednisolone) (e.g. 40-80 mg/mL), dexamethasone, and mixtures thereof.

The system components (e.g., cannula, stylets, syringe, etc.) may be disposable or sterilisable for re-use. Sterilization can be done via radiation, e.g. gamma radiation or electronic beam radiation, or via gas sterilization, such as, for example, with ethylene oxide or steam sterilization. The radiation can be performed in a terminal sterilization step in the final packaging or the individual components can be sterilized separately and the final package assembled in a sterile environment.

It will be apparent to those skilled in the art that various additional modifications and variations can be made to the embodiments described herein without departing from the invention as described and claimed.

The invention claimed is:

1. A method of delivering a drug depot to a site within a patient, the method comprising:
   a. inserting a cannula with a solid stylet received into a target tissue of the patient under image guidance;
   b. retaining the drug depot at a distal end of a delivery stylet such that initially only a first portion of the drug depot is positioned inside the delivery stylet and a second portion of the drug depot protrudes from the distal end of the delivery stylet and fluidic pressure is required to subsequently eject the first portion of the drug depot from the delivery stylet;
   c. removing the solid stylet from the cannula and inserting the delivery stylet into the cannula until a distal portion of the delivery stylet emerges from a distal end of the cannula;
   d. positioning the drug depot under image guidance by moving the delivery stylet forwards and/or backwards until the drug depot is positioned at a desired location; and
   e. actuating an actuator to expel the drug depot from the delivery stylet.

2. The method of claim 1, comprising delivering the drug depot comprising a therapeutically acceptable amount of a growth modulator into a first epiphyseal growth plate of a first vertebra for altering the growth of the first epiphyseal growth plate to correct or compensate for disproportionate growth, wherein the method is for treating scoliosis.

3. A method of delivering a drug depot to a site within a patient, the method comprising:
   a. inserting a hollow cannula into a target tissue of the patient under image guidance;
   b. retaining the drug depot at a distal end of the a delivery stylet such that initially only a first portion of the drug depot is positioned inside the delivery stylet and a second portion of the drug depot protrudes from the distal end of the delivery stylet and fluidic pressure is required to subsequently eject the first portion of the drug depot from the delivery stylet;
   c. inserting the delivery stylet into the hollow cannula until the distal end of the delivery stylet emerges from a distal end of the hollow cannula;
   d. positioning the drug depot under image guidance by sliding the delivery stylet within the hollow cannula until the drug depot is positioned at a desired location; and
   e. actuating an actuator to expel the first portion of the drug depot from the distal end of delivery stylet, thereby depositing the drug depot at the desired location.

4. The method of claim 3 further comprising attaching the actuator to the delivery stylet after positioning the drug depot at the desired location.

5. The method of claim 3, the actuating further comprising delivering fluid from the actuator to an interior of the delivery stylet to create fluidic pressure within the delivery stylet sufficient to eject the drug depot therefrom.

6. The method of claim 5, delivering fluid further comprising delivering a liquid.

7. The method of claim 6, the liquid comprising an agent selected from the group consisting of an anaesthetic, Depo-Medrol (methylprednisolone), dexamethasone, and mixtures thereof.

8. The method of claim 3 wherein the drug depot comprises an oval solid form.

9. The method of claim 3 wherein the drug depot comprises a spherical solid form.

10. The method of claim 3 further comprising:
    inserting a solid stylet into the hollow cannula to provide rigidity thereto prior to inserting
    the hollow cannula into the target tissue; and
    removing the solid stylet from the cannula prior to inserting the delivery stylet into the hollow cannula.

11. The method of claim 3 wherein the drug depot comprises a radiographic marker.

12. The method of claim 11 further comprising visualizing the drug depot under a diagnostic imaging beam or modality.

13. The method of claim 12 wherein the diagnostic imaging beam or modality is selected from the group consisting of computed tomography (CT), ultrasound, x-ray, magnetic resonance imaging (MRI), and fluoroscopy.

14. The method of claim 3 wherein at least one of the hollow cannula and the delivery stylet comprises a radiopaque material or ultrasound responsive topography to provide increased contrast relative to an absence of the radiopaque material or ultrasound topography under a diagnostic imaging beam.

15. The method of claim 3, the method further comprising delivering the drug depot comprising a therapeutically acceptable amount of a growth modulator into a first epiphyseal growth plate of a first vertebra for altering the growth of the first epiphyseal growth plate to correct or compensate for disproportionate growth, wherein the method is for treating scoliosis.

\* \* \* \* \*